(12) United States Patent
Mackay

(10) Patent No.: US 10,456,554 B2
(45) Date of Patent: Oct. 29, 2019

(54) DEVICE DELIVERY CATHETER HAVING A CURVED DISTAL TIP

(75) Inventor: Allen B. Mackay, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 313 days.

(21) Appl. No.: 12/105,211

(22) Filed: Apr. 17, 2008

(65) Prior Publication Data

US 2009/0264980 A1 Oct. 22, 2009

(51) Int. Cl.
*A61M 25/00* (2006.01)
*A61F 2/95* (2013.01)

(52) U.S. Cl.
CPC ........... *A61M 25/0068* (2013.01); *A61F 2/95* (2013.01); *A61M 25/0041* (2013.01); *A61F 2002/9505* (2013.01); *A61F 2002/9511* (2013.01); *A61M 25/008* (2013.01); *A61M 25/0069* (2013.01)

(58) Field of Classification Search
CPC ............... A61F 2/97; A61F 2002/9505; A61F 2002/9511; A61F 2/95; A61M 25/0041; A61M 25/0068; A61M 25/0069
USPC ............................................... 623/1.11, 1.12
See application file for complete search history.

(56) References Cited

U.S. PATENT DOCUMENTS

| | | | |
|---|---|---|---|
| 5,147,334 A | 9/1992 | Moss | |
| 6,045,557 A * | 4/2000 | White et al. | 606/108 |
| 6,113,579 A | 9/2000 | Eidenschink et al. | |
| 6,224,627 B1 | 5/2001 | Armstrong et al. | |
| 6,293,924 B1 | 9/2001 | Bagaoisan et al. | |
| 6,322,586 B1 | 11/2001 | Monroe et al. | |
| 6,383,171 B1 * | 5/2002 | Gifford et al. | 604/508 |
| 6,544,218 B1 | 4/2003 | Choi | |
| 6,551,350 B1 * | 4/2003 | Thornton et al. | 623/1.13 |
| 6,613,081 B2 * | 9/2003 | Kim et al. | 623/1.15 |
| 6,827,731 B2 * | 12/2004 | Armstrong et al. | 623/1.12 |
| 7,115,134 B2 | 10/2006 | Chambers | |
| 2003/0088305 A1 * | 5/2003 | Van Schie | A61F 2/06 623/1.12 |
| 2004/0106974 A1 * | 6/2004 | Greenberg et al. | 623/1.11 |
| 2004/0116832 A1 * | 6/2004 | Friedrich et al. | 600/585 |
| 2005/0244955 A1 | 11/2005 | Li | |
| 2007/0088424 A1 | 4/2007 | Greenberg et al. | |
| 2007/0099218 A1 | 5/2007 | Ho | |
| 2007/0270781 A1 | 11/2007 | Burgermeister et al. | |
| 2008/0300666 A1 | 12/2008 | Heidner et al. | |
| 2013/0012924 A1 | 1/2013 | Davis et al. | |

FOREIGN PATENT DOCUMENTS

| | | |
|---|---|---|
| EP | 1 136 044 | 9/2001 |
| WO | 2006119806 A1 | 11/2006 |
| WO | 2007057718 A2 | 5/2007 |

(Continued)

OTHER PUBLICATIONS

International Search Report and Written Opinion from PCT/US2009/002397, dated Jul. 8, 2009, 10 pages.

*Primary Examiner* — Martin T Ton

(57) ABSTRACT

A catheter for delivery of intraluminal and expandable devices. The catheter is provided with a flexible curved tip distal to the device loaded onto the catheter for delivery to a desired site within a body conduit. The curved distal tip causes the catheter to rotate to a preferred rotational orientation, which may be desirable for any device having asymmetric features, particularly when used in tortuous body conduits.

2 Claims, 5 Drawing Sheets

(56) References Cited

FOREIGN PATENT DOCUMENTS

| WO | 2007/084724 | 7/2007 |
| WO | 2007/092276 | 8/2007 |
| WO | 2008/140796 | 11/2008 |

* cited by examiner

DEVICE DELIVERY CATHETER HAVING A CURVED DISTAL TIP

FIELD OF THE INVENTION

The present invention relates to apparatus and methods for delivery of intraluminal devices such as stents, stent-grafts or ultrasound arrays to a desired site.

BACKGROUND OF THE INVENTION

Treatment and diagnosis of diseases of human vascular, digestive and other systems has been evolving from using open type surgical procedures to using newer minimally invasive techniques. The minimally invasive techniques generally involve placing a stent, stent-graft or ultrasound array into the lumen of a patient's diseased vessel. In the case of a vessel that has a reduced cross-sectional area due to disease, flow of bodily fluids through that vessel may be reduced or even prevented. Alternatively stents and stent-grafts may be used in the repair of aneurysmal vessels. An intraluminal device such as a stent or stent-graft placed into the diseased vessel can help return the vessel to pre-disease flow conditions by restoring the vessel to a more normal luminal configuration. Additionally, a stent-graft may prevent tissue in-growth from a diseased area migrating into an area of healthy tissue.

Intraluminal devices such as stents or stent-grafts can be generally grouped into two categories. One category includes devices that are assembled on top of an expanding means such as a balloon. When the device is delivered to the desired position within the anatomy, the balloon is expanded, causing the device to permanently expand to a larger diameter. The intraluminal device is then ductile enough so that it plastically deforms and remains in place in the anatomy when expanded. The other category of devices relates to "self-expanding" devices which are delivered to the desired site in the anatomy in a radially compressed state with some type of constraining means to prevent them from expanding until the clinician desires. Control of this "self-expansion" may be through many different methods. One method to control the "self-expansion" is through constraining the device with a sheath which can be actuated by the clinician when it is desired to release the constrained device for deployment. Such constraining sheaths, for example, may include one or more seams that can be remotely released via a pull line or other similar coupling member actuated by the clinician. When the seam is released, the self-expanding device is deployed, expanding to a larger diameter until contacting the luminal wall of the vessel.

Intraluminal devices such as stents or stent-grafts are generally delivered to the site of the disease via a catheter. Some disease sites are accessible with a short, relatively stiff catheter with an intraluminal device located near the distal end. These catheters are suitable, for example, where a percutaneous puncture is made for insertion of the catheter relatively close to the disease site. In these cases the catheter may be directly manipulated by the physician from the proximal end outside of the body. The physician may move the catheter longitudinally and rotationally in the proximity of the disease site until the device to be deployed is in its desired location.

In contrast, when the catheter insertion site is distant from the disease site, the catheter must be long and relatively flexible to allow navigation through tortuous anatomy and simultaneously suitably stiff for pushability to enable the catheter to be guided into place over a guidewire. This type of catheter may also have an intraluminal device loaded near its distal end. With this type of catheter, precise longitudinal (axial) and rotational control of the position of the device by the physician is made more difficult due to the length and flexibility of the catheter.

Possible references of interest may include U.S. Pat. No. 6,224,627 to Armstrong et al., U.S. Pat. No. 6,551,350 to Thornton et al. and US Published Patent Application 2007/0270781A1 to Burgermeister et al.

SUMMARY OF THE INVENTION

The present system is a catheter apparatus for delivering an intraluminal device in desired axial position and rotational orientation with respect to the anatomy at the target site. The system may include an asymmetric feature such as a side-branch port, a constraining sheath having a seam extending along one side of its length, a practitioner actuated deployment line, a directional ultrasound array, etc. Controlled orientation of asymmetric features such as these may be particularly useful for various situations such as treatment of vessel side branches or any other situation where a particular orientation of an asymmetric feature is advantageous.

Expandable intraluminal devices that may be delivered and deployed by the present system may include, but are not limited to self-expanding stents and stent-grafts, balloon expandable stents and stent-grafts, embolic filters, vena cava filters, etc.

The remote nature of some target sites may make it challenging to control the rotational orientation of the catheter. In the process of delivering an intraluminal device to a target anatomical site, it may be required to pass the device through various body conduits that includes tortuous bends. The action of moving the device through these bends may place uncontrolled torsional forces on the device thereby causing it to rotate undesirably. Due to this rotation and the flexibility of the catheter, the orientation of the delivery catheter at the target site is unpredictable or difficult to control. For some types of delivery and deployment systems it may be desirable to control the rotational position of the device relative to vessel curvature and/or side-branch location, etc.

With the present system, a torque or rotational force is imparted to the catheter and device each time the distal tip portion of the system passes through a curvature in the anatomy. This torque acts to maintain the rotational positioning of the catheter and the device with respect to the vessel curvature. In this fashion, rotational positioning of an asymmetric feature (such as the seam on the deployment covering) with respect to the vessel curvature is maintained.

The present system is passive, therefore requiring substantially no input or manipulation from the clinician to maintain the proper orientation between the seam of the deployment covering on a self-expanding device and the vessel curvature. The ability of the present system to provide desired rotational orientation is achieved by providing the system with a distal tip that is pre-configured to have a curved shape when no external forces are applied to the tip. This curved shape is made to curve progressively away from one side of the longitudinal axis of the straight catheter (moving in a distal direction). The curved distal tip is preferably progressively tapered from a larger outside diameter at its proximal end to a smaller outside diameter at its distal end. The distal tip is defined to be only the portion of the system that is distal to any device which is mounted on the catheter. This distal tip contains a lumen along its length for passage of a guidewire.

The distal tip in this system is preferably flexible. Flexibility allows the curved tip to be straightened to an extent when placed over a guidewire. Correspondingly, curvature may be simultaneously imparted to the guidewire by the distal tip. When mounted on a guidewire, the present system with the flexible distal tip may be more easily guided through tortuous anatomy or narrow passages caused by strictures or lesions. However, even when substantially straightened by the guidewire the distal tip maintains its ability to create a rotational force on the catheter. This rotational force is generated any time the distal tip encounters curvature in the anatomy that deforms the tip away from its unconstrained curvature. This rotational force can be used to maintain the rotational orientation of an asymmetric feature on a device and/or delivery system to the vessel wall.

This system also introduces a bias to the direction of the guidewire as the system is inserted into the vasculature. With most guidewire device delivery systems, when a curved vasculature is encountered during advancing the guidewire or the catheter, the distal ends of the guidewire and the catheter tend to remain straight, bringing the catheter tip and the carried device close to outside radius of the vessel wall. With the present system, the flexible curved distal tip encourages the guidewire to bias towards the inner radius of a curved vessel, thereby allowing the device to progress in a forward direction while remaining closer to the center of the vessel. This is important when strictures or lesions may be present within the vessel in order to enable safe passage of the device through the restriction.

DETAILED DESCRIPTION OF THE DRAWINGS

The present catheter-based device delivery system achieves a preferred rotational orientation in the positioning of an intraluminal medical device loaded onto the distal end of the system with minimal manipulation from the operator at the proximal end. Proximal refers to locations that are closer to the end of the catheter to which the hub assembly is attached. Distal refers to locations that are further away from the hub assembly. By attaching a flexible curved tip, which possesses a pre-configured curved form when no external forces are applied, to the distal end of a device delivery catheter, the system is provided with the ability to preferentially rotate in response to the guidewire curvature or to contact with the luminal surface of a curved body conduit. This rotational positioning occurs with substantially no control input from the operator.

This system also allows for the low-profile delivery of a self-orienting catheter as the flexible distal tip straightens to an extent when placed over a guidewire. Also, this system biases the catheter distal tip away from the outside radius of a curved vessel when it is being introduced into the vessel on a guidewire.

The present delivery system allows for the most favorable rotational orientation of an asymmetric feature associated with a delivered device, such as a releasing seamline on a constraining sheath provided about the outer surface of a self-expanding device held in a constrained state. Likewise, a remotely operated pull line or coupling member used to remotely release this seam is maintained in the preferred orientation, i.e., along the inner radius of a curved body conduit.

Figure 1A:
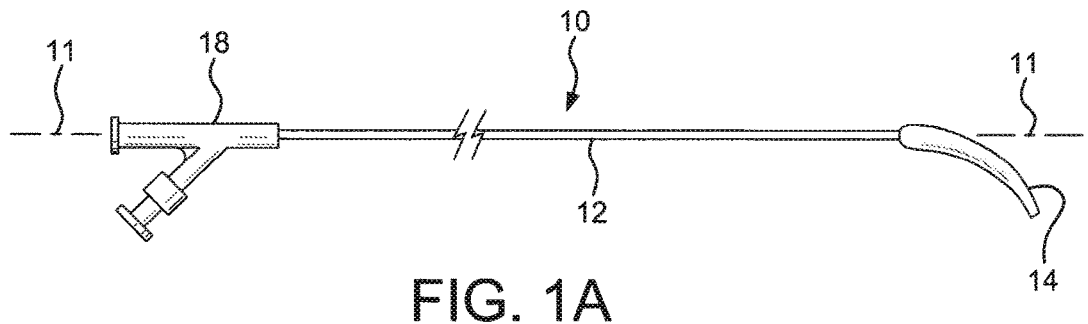
FIG. 1A is a plan view of a catheter assembly with a flexible curved distal tip.

One embodiment of the distal tip is illustrated in FIG. 1A, which shows a catheter-based delivery system 10 with a catheter 12 having a hub assembly 18 affixed to the proximal end by which a practitioner exerts control on the system 10 and a flexible, curved distal tip 14 secured to the opposite end. A distal tip 14 is defined as being a tip portion positioned distal to any device which may be mounted onto the catheter 12. The distal tip 14 is pre-configured to have a curved or arcuate shape when unaffected by external forces. This curved shape is made to curve progressively away from one side of the longitudinal axis 11 of the straight catheter 12 (moving in a distal direction).

Figure 1B:
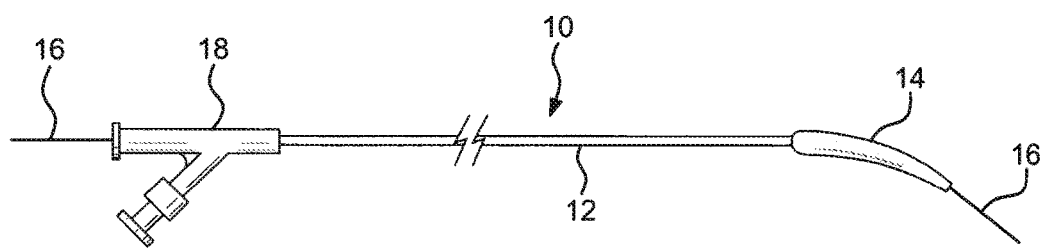
FIG. 1B is a plan view of a catheter assembly with guidewire inserted into the catheter lumen.

FIG. 1B shows the catheter-based system 10 having a guidewire 16 inserted through a first lumen of the catheter 12. FIG. 1B illustrates the flexibility of the curved distal tip 14 which allows it to reconfigure from the previous relatively small radius curved shape into a somewhat less curved shape. This less curved shape reduces the profile of the distal tip 14 when it is positioned and manipulated over the guidewire 16. The decreased profile assumed by the distal tip 14 when it is positioned on a guidewire 16 is advantageous when the catheter is advanced through vasculature containing strictures or lesions that reduce the diameter of the vessel lumen.

Figure 1C:
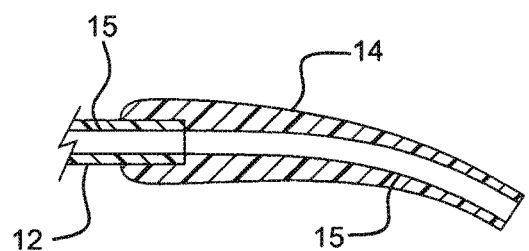
FIG. 1C is a longitudinal cross section of the curved distal tip as attached to a catheter shaft.

FIG. 1C shows a longitudinal cross section of curved distal tip 14 attached to the distal end of catheter 12. Guidewire lumen 15 extends through catheter 12 and distal tip 14.

Flexible curved distal tip 14 may be made from a variety of materials including polymeric elastomers such as silicone, various polyurethanes or polyether block amides (e.g., Pebax® from Arkema Inc., Philadelphia Pa. 19103). While distal tip 14 may be manufactured in a variety of ways, a preferred technique is by injection molding. A preferred method of attaching the distal tip 14 to the distal end of catheter 12 involves heat bonding. Various other methods of attachment are possible including solvent welding and the use of various adhesives.

U.S. Pat. No. 6,551,350 to Thornton et al. teaches the manufacture of a delivery system for delivering implants or devices such as stents or stent-grafts that includes a restraining member that is adapted and configured for surrounding at least a portion of a collapsed or compressed implant and a coupling member for releasably coupling portions of the restraining member to one another to maintain the implant in its collapsed or compressed state.

Figure 2A:
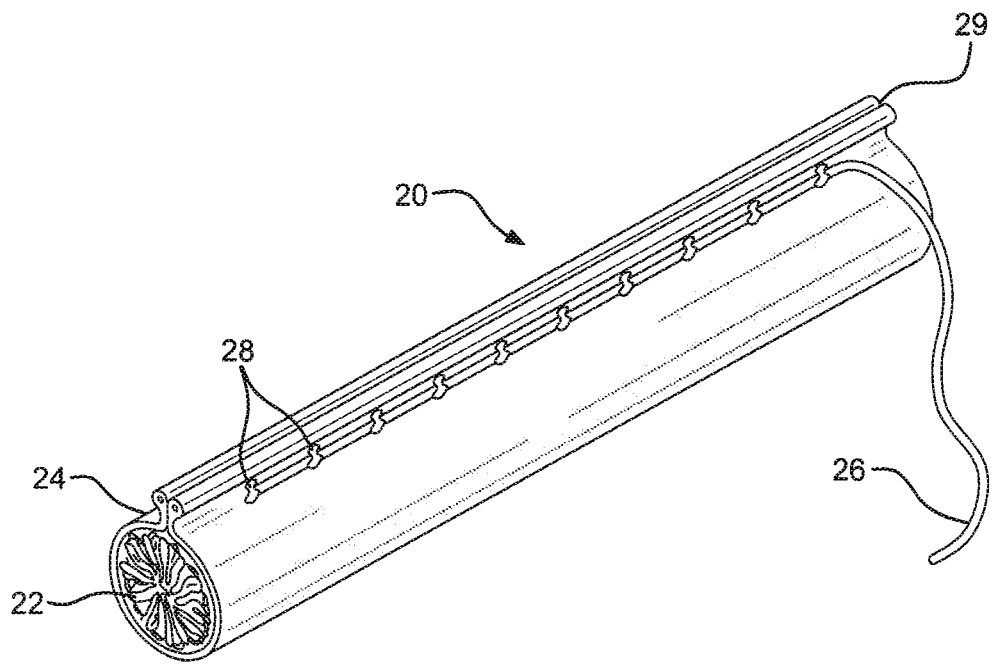
FIG. 2A is a perspective view of an expandable intraluminal device contained in a diametrically compacted state by a constraining system.
Figure 2B:
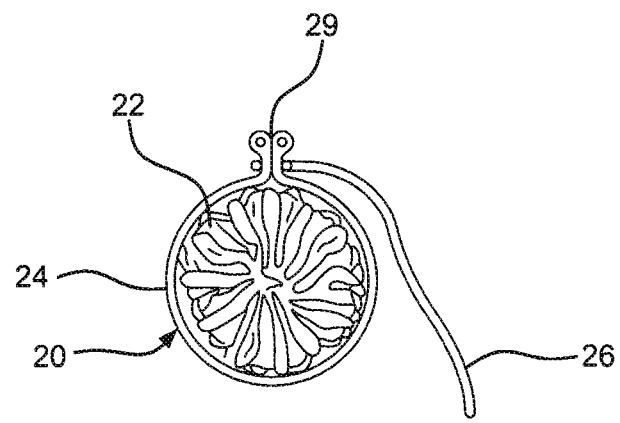
FIG. 2B is an end view of an expandable intraluminal device contained in a diametrically compacted state by a constraining system.

FIGS. 2A and 2B illustrate an embodiment of a restraining system 20 of the prior art such as taught by Thornton et al. which includes a device 22 which is constrained by a restraining (or constraining) member 24. The restraining member 24 has a coupling member or pull line 26 for releasably coupling portions of the restraining member 24 to each other. Through holes 28 are disposed along two opposing edges of the restraining member 24 so that the coupling member 26 may be laced or threaded therethrough with a stitch releasable by the application of tension to an end of the coupling member or line 26 with which the stitch is created. The stitching of the opposing edges of restraining member 24 by coupling member 26 thus forms a disruptable seamline 29. The application of tension to the free end of coupling member 26 releases the stitched edges of the restraining member 24 which in turn frees device 22 for deployment.

Figure 3A:
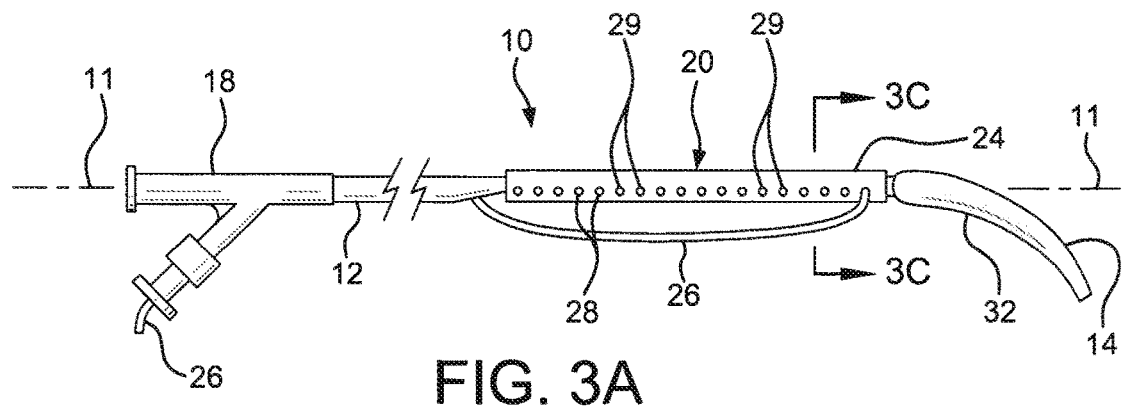
FIG. 3A is a plan view of a restraining system mounted on a catheter based delivery system having a flexible, pre-configured distal tip.
Figure 3B:
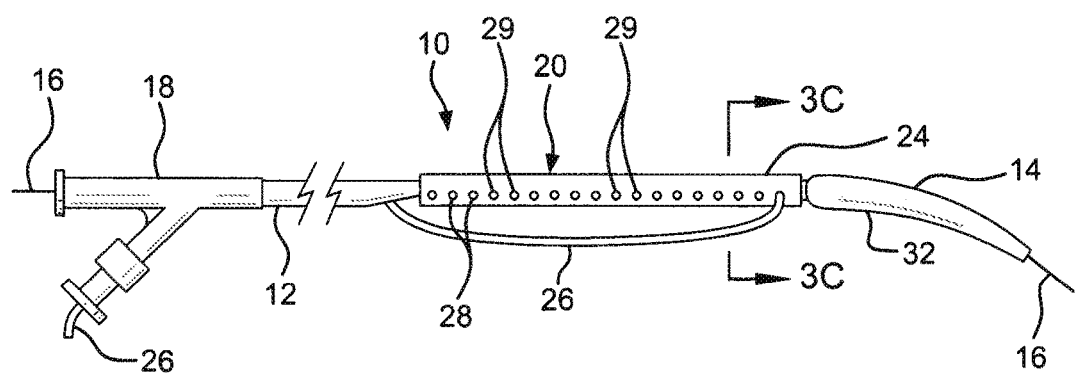
FIG. 3B is a plan view of a restraining system mounted on a catheter based delivery system with a guidewire inserted into a catheter lumen.

As shown in FIGS. 3A and 3B, the restraining system 20 (including constrained device 22) may be mounted on a catheter-based delivery system 10. The restraining system 20 has a restraining member 24 with through holes 28 and a coupling member 26. It is understood that the restraining member 24 is not limited to the restraining member illustrated and may include pull back sheaths, perforated or tearable sheaths, rolling or everting membranes, and the like. It is further understood that the device 22 can be any manner of device including any that are suitable for implantation in the human body. Remotely operated coupling member 26 releasably couples portions of the restraining member 24 to each other thereby constraining device 22 in a compacted state. Coupling member 26 exits the second lumen of catheter 12 at the proximal end of restraining system 20. Through holes 28 that form the disruptable seamline 29 of restraining member 24 are substantially aligned along the inner meridian (i.e., inner radius) 32 of the arc created by the curvature of the distal tip 14. By substantially aligned with the inner meridian of the curved distal tip is meant that the seamline 29 is aligned within about 15 radially disposed degrees (measured from the longitudinal axis 11 of constrained device 20 as the center of rotation of the measured angle) from the inner meridian 32. In FIG. 3B the distal tip 14 is shown in a less curved state due to a straightening force applied by the guidewire 16 inserted through the lumen of the curved distal tip 14.

It is apparent that the present system also allows for alignment of an asymmetric feature in other entirely different specific relationships with respect to the inner meridian 32 of distal tip 14. For example, a feature (such as an ultrasound array) may be oriented 90 degrees away from the inner meridian, or 180 degrees away from the inner meridian.

Figure 3C:
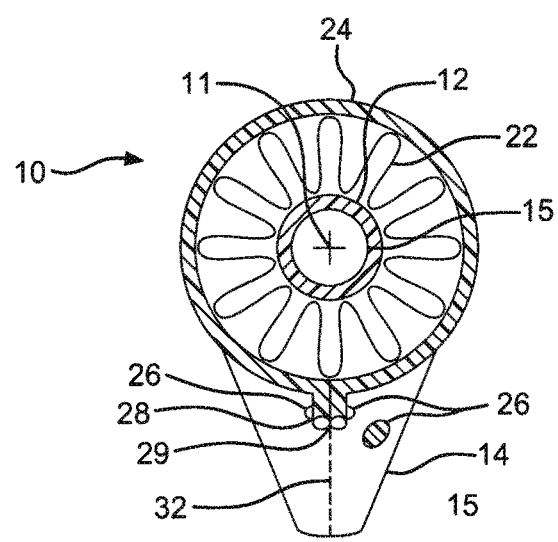
FIG. 3C is an enlarged transverse cross sectional view taken through the constrained device, looking toward the distal tip and showing the asymmetric feature substantially aligned with the inner meridian of the curved distal tip.

FIG. 3C is an enlarged transverse cross sectional view taken through the constrained device 22, looking toward the distal tip 14 and showing the asymmetric feature (e.g., through holes 28, coupling member 26 or seamline 29) substantially aligned with the inner meridian 32 of the curved distal tip 14.

The mounting of restraining system 20 on catheter 12 typically reduces the flexibility of catheter 12 for the length of restraining system 20. The flexibility of curved distal tip 14 is thus of even greater importance for navigating the system 10 along a desired path.

Figure 4:
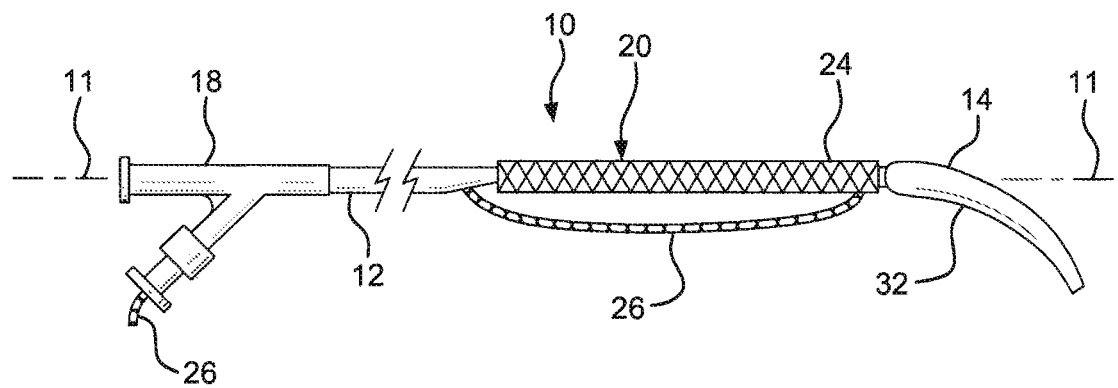
FIG. 4 is a plan view of a restraining system with a contiguous coupling member mounted on a catheter based delivery system having a flexible, pre-configured distal tip.

FIG. 4 illustrates another embodiment of a device 22 provided with an alternative restraining system 20 as mounted on a catheter-based delivery system 10 generally as taught in U.S. Pat. No. 6,224,627 to Armstrong et al. According to this type of restraining system 20 a thin multiple filament (film or fiber) structure can hold high internal pressures but when desired an extension of the filaments can be pulled to unfurl the restraining system 20 to release device 22 for deployment.

While FIGS. 3A, 3B and 4 depict two configurations in which a restraining system 20 is preferably mounted with coupling member 26 aligned along the inner meridian of the arc created by the curvature of the distal tip 14, it is appreciated that coupling member 26 may alternatively be positioned at other rotational positions relative to the inner meridian 32 of distal tip 14.

Figure 5:
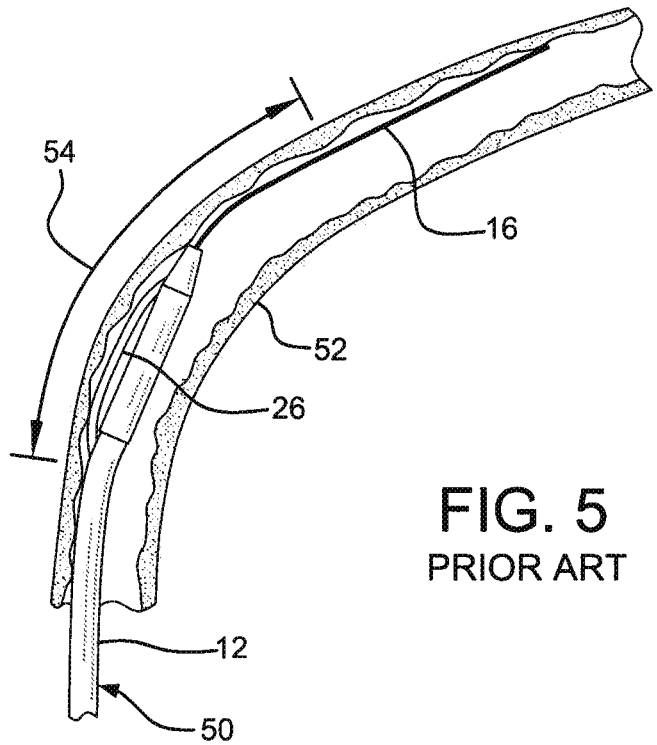
FIG. 5 is a plan view of a prior art device delivery system that does not have a flexible, pre-configured distal tip, shown inserted into a curved vessel and guided with a guidewire.

FIG. 5 shows a prior art delivery system 50 (which does not have a flexible, curved distal tip) that has been inserted over a guidewire 16 into a vessel 52 with curvature 54. When guidewire 16 is inserted into such a vessel 52 that has curvature 54, the tendency is for the guidewire 16 to bias toward to the outer meridian of the vessel 52 due to guidewire 16 wanting to retain its normal straight configuration. Catheter 12, delivered subsequent to the guidewire 16, is even stiffer and as such also exhibits this same tendency. As FIG. 5 illustrates, since guidewire 16 tends toward the outside meridian of the curved vessel, the device delivery system 50 which is advancing over the guidewire 16 also tracks toward the outside meridian of the vessel 52. This tendency for the guidewire 16 and catheter 12 to bias towards the outside radius of the vessel 52 can be problematic when a stricture or lesion is encountered.

FIG. 5 also shows how coupling member 26 may arbitrarily end up on the outer meridian (or any other circumferential location) for a prior art system. This is undesirable at the location intended for deployment as the application of tension necessary to initiate deployment causes coupling member 26 to want to assume the shortest length, i.e. to move to the inner meridian of curved vessel 52. If coupling member 26 is not located at the inner meridian to begin with, the result is an unnecessary increase in system friction and an increase in the tensile force necessary to cause device deployment.

Figure 6A:
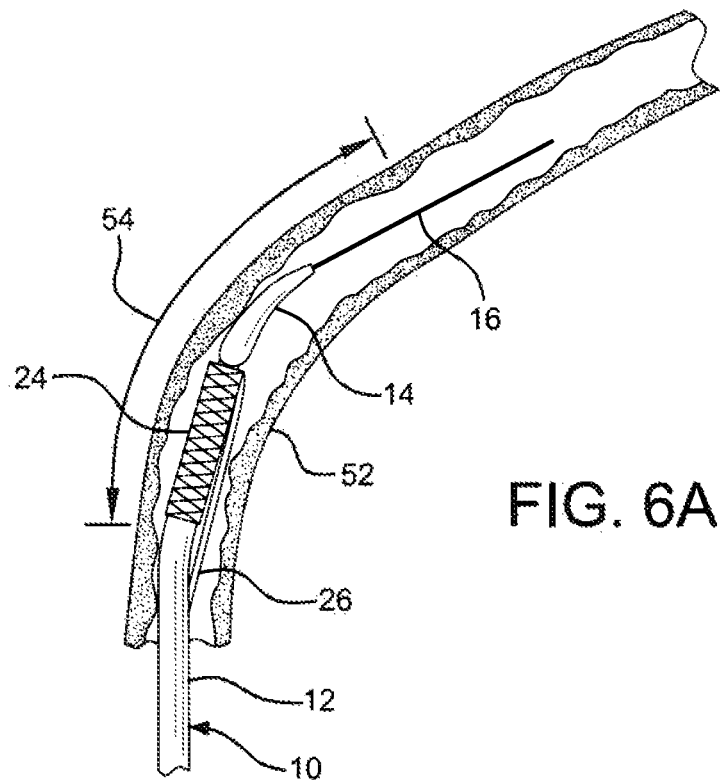
FIG. 6A is a plan view of the present catheter-based delivery system having a flexible, curved distal tip and a restraining system with a coupling member (pull line) shown inserted into a curved vessel and guided with a guidewire.

FIG. 6A illustrates the present catheter-based delivery system 10 which includes flexible curved distal tip 14 that has been inserted over guidewire 16 into a vessel 52 with curvature 54. System 10 has a restraining member 24 which incorporates a coupling member 26. Due to the force applied to the guidewire 16 by the self-orienting flexible curved distal tip 14, the guidewire 16 is biased toward the inside meridian of the vessel 52 offsetting its tendency to straighten and tend toward the outside meridian of the wall of vessel 52. System 10, which is advancing over the guidewire 16 then also tends toward the inside meridian of the vessel 52, lessening the problems which may be associated with negotiating through strictures or lesions which may reside within the vessel 52. Likewise, due to the self-orienting rotational capability of system 10 due to the rotational force generated by curved distal tip 14 when it enters a curved vessel, coupling member 26 is aligned along the inner meridian of the curvature of vessel 52. This alignment minimizes the tensile force necessary to cause deployment of device 22.

FIG. 6A further shows that the self-orienting distal tip 14 has been straightened to an extent by guidewire 16. Surprisingly, even though the self-orienting flexible curved distal tip 14 has been somewhat straightened by the guidewire 16, it still creates a torque or rotational force on the catheter as it is advanced over a guidewire that has been previously inserted through curved vasculature. As previously described, the catheter 12 and any device 22 mounted on it then has a tendency to rotationally move so that the self-orienting curved distal tip 14 moves to position itself aligning its curvature with the curvature of vessel 52. In other words, the curved distal tip 14 has a most favorable orientation that results from its ability to return to its lowest stored-energy state.

Figure 6B:
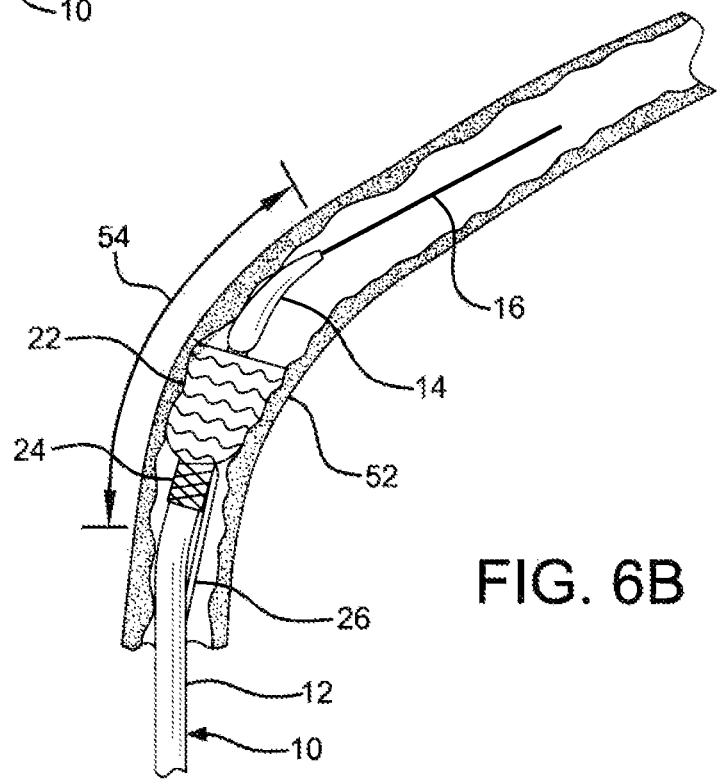
FIG. 6B is a plan view of the catheter-based delivery system of FIG. 6A during deployment of a delivered intraluminal expandable device.

FIG. 6B shows the device delivery system 10 wherein restraining member 24 has been partially removed allowing the deployment of the device 22, into the vessel 52.

EXAMPLE

A Gore VIABAHN® delivery catheter (W. L. Gore & Associates, Newark, Del., part number VBC 081501) was obtained which included a device pre-loaded and constrained on one end. A steel mandrel of diameter that was only slightly smaller than the inside diameter of the catheter was inserted into the guidewire lumen from the distal end until it extended proximally beyond the device supplied with the catheter assembly. The supplied distal tip was heated and removed using a Hotshot 1 kW radio frequency welder (Ameritherm Inc., Scottsville, N.Y.). The catheter tubing extended distally for about 7 mm beyond the constrained device. The straight mandrel was withdrawn from the catheter in a distal direction. A curved mandrel was inserted into the catheter tubing positioned to obtain the desired curvature. The mandrel was sized to the inner diameter of the catheter tubing, and was curved at the site where the curved tip was to be positioned, with the curvature matching the desired curvature of the distal tip. A curved distal tip was formed by injection molding using 4033 PEBAX® (Arkema Inc., Philadelphia, Pa.). The curved tip had a radius of 16 mm and a length of 22 mm. Following injection molding, the tip was positioned over the mandrel and catheter tubing, and adjacent to the constrained stent. The inner meridian of the curved tip was aligned rotationally with the deployment line created by the multiple filament braid that formed the restraining sheath disposed about the constrained device. The tip was then heated using the radio frequency welder to bond to the exposed distal shaft of the catheter. The tip was then cooled with an air stream and the curved mandrel was removed. The device was tested using a curved tubular test fixture incorporating a 180 degree bend, the bend having a 3.5 cm radius. This fixture was made using a transparent tube having an inside diameter of 5 mm. A guidewire was inserted through the test fixture and the catheter was tracked over the guidewire. The catheter was inserted into the tubular fixture a number of times such that the deployment line was aligned with varying orientations relative to the curvature. Each test resulted in the catheter rotating to orient the deployment line to the inside of the curvature.

While particular embodiments of the present invention have been illustrated and described herein, the present system should not be limited to such illustrations and descriptions. It should be apparent that changes and modifications may be incorporated and embodied as part of the present system within the scope of the following claims.

What is claimed is:

1. A catheter comprising:
    a catheter shaft having a proximal end, a distal end, an intermediate section between the proximal end and the distal end, and a curved surface reducing a diameter of the catheter shaft at the intermediate section, the catheter shaft having a central lumen and defining a central longitudinal axis;
    a tip secured to the distal end of the catheter shaft, the tip being flexible and having a first end, a second end, and a central longitudinal axis extending between the first and second ends, the longitudinal axis of the tip defining an arcuate shape in the unbiased state, the arcuate shape having a concave side and a convex side; and
    a device secured to the catheter shaft at the intermediate section, the device including a restraining system including a constraining sheath and a release line for releasing the constraining sheath, the restraining system being mounted such that the release line exits the catheter shaft at the curved surface of the catheter shaft and extends toward the tip and is maintained in longitudinal alignment with the concave side of the arcuate shape defined by the longitudinal axis of the tip.

2. The catheter of claim 1, wherein the constraining sheath defines a seam, the release feature includes is a pull line releasably coupling the sheath together along the seam, and the seam is maintained in longitudinal alignment with the concave side.

* * * * *